(12) United States Patent
Prince et al.

(10) Patent No.: US 11,285,276 B2
(45) Date of Patent: Mar. 29, 2022

(54) CONTROL DEVICE FOR A MEDICAL AEROSOL DELIVERY DEVICE

(71) Applicant: KONINKLIJKE PHILIPS N.V., Eindhoven (NL)

(72) Inventors: Ivan Prince, Chichester (GB); Neal McLoughlin, Bognor Regis (GB)

(73) Assignee: Koninklijke Philips N.V., Eindhoven (NL)

( * ) Notice: Subject to any disclaimer, the term of this patent is extended or adjusted under 35 U.S.C. 154(b) by 627 days.

(21) Appl. No.: 15/736,852

(22) PCT Filed: Jun. 29, 2016

(86) PCT No.: PCT/EP2016/065188
§ 371 (c)(1),
(2) Date: Dec. 15, 2017

(87) PCT Pub. No.: WO2017/001509
PCT Pub. Date: Jan. 5, 2017

(65) Prior Publication Data
US 2018/0169356 A1 Jun. 21, 2018

(30) Foreign Application Priority Data
Jun. 30, 2015 (EP) .................................. 15174429

(51) Int. Cl.
*A61M 16/00* (2006.01)
*A61M 15/00* (2006.01)
*A61M 11/00* (2006.01)

(52) U.S. Cl.
CPC ...... *A61M 15/0066* (2014.02); *A61M 11/003* (2014.02); *A61M 11/005* (2013.01);
(Continued)

(58) Field of Classification Search
CPC ............ A61M 15/0066; A61M 11/003; A61M 16/024; A61M 11/005; A61M 2016/0039;
(Continued)

(56) References Cited

U.S. PATENT DOCUMENTS 5,201,322 A * 4/1993 Henry ..................... A61B 5/087
310/338
5,365,922 A * 11/1994 Raemer ................ A61B 5/0833
128/202.22
(Continued)

FOREIGN PATENT DOCUMENTS

CN 101125083 A 2/2008
EP 0765631 A2 4/1997
(Continued)

*Primary Examiner* — Samchuan C Yao
*Assistant Examiner* — Nathan M Le
(74) *Attorney, Agent, or Firm* — Daniel H. Brean

(57) ABSTRACT

The invention relates to a control device (10) for a medical aerosol delivery device (2), a medical aerosol delivery system (1), a method for controlling a medical aerosol delivery device (2), a computer program element for controlling such device or system, and a computer readable medium having stored such computer program element. The control device (10) for a medical aerosol delivery device (2) comprises a provision unit (11), a processing unit (12), and a control unit (13). The provision unit (11) is configured to provide inhalation length data per breath. The processing unit (12) is configured to compare the provided inhalation length data with a predetermined inhalation length threshold, and to filter provided inhalation length data below the predetermined inhalation length threshold. The control unit (13) is configured to control the medical aerosol delivery device (2) based on the filtered inhalation length data.

4 Claims, 3 Drawing Sheets

(52) U.S. Cl.
CPC .... *A61M 15/0065* (2013.01); *A61M 15/0085* (2013.01); *A61M 16/024* (2017.08); *A61M 2016/0039* (2013.01); *A61M 2205/3334* (2013.01); *A61M 2205/50* (2013.01); *A61M 2230/40* (2013.01)

(58) Field of Classification Search
CPC ...... A61M 2205/3334; A61M 2205/50; A61M 2230/40; A61M 15/0065; A61M 15/0085
See application file for complete search history.

(56) References Cited

U.S. PATENT DOCUMENTS

| | | | |
|---|---|---|---|
| 5,419,315 A * | 5/1995 | Rubsamen | A61M 15/0065 128/200.14 |
| 5,826,570 A | 10/1998 | Goodman | |
| 5,944,680 A * | 8/1999 | Christopherson | A61B 5/03 128/897 |
| 6,237,589 B1 | 5/2001 | Denyer | |
| 6,367,470 B1 * | 4/2002 | Denyer | A61M 15/0065 128/200.14 |
| 6,537,228 B1 | 3/2003 | Lambert | |
| 8,297,280 B2 | 10/2012 | Watanabe | |
| 8,464,706 B2 | 6/2013 | Crockford et al. | |
| 9,135,397 B2 | 9/2015 | Denyer et al. | |
| 10,130,779 B2 | 11/2018 | Denyer et al. | |
| 2005/0107658 A1 * | 5/2005 | Brockway | A61M 60/50 600/16 |
| 2005/0183725 A1 | 8/2005 | Gumaste | |
| 2007/0125370 A1 * | 6/2007 | Denyer | A61M 15/00 128/200.14 |
| 2008/0188796 A1 * | 8/2008 | Steil | A61B 5/14865 604/66 |
| 2009/0314292 A1 * | 12/2009 | Overfield | A61M 15/0065 128/203.15 |
| 2012/0059353 A1 * | 3/2012 | Kovatchev | A61B 5/0002 604/504 |
| 2013/0289431 A1 | 10/2013 | Gavish | |
| 2013/0324872 A1 * | 12/2013 | Babaeizadeh | A61M 16/021 600/532 |
| 2014/0261414 A1 | 9/2014 | Weitzel | |
| 2016/0114115 A1 * | 4/2016 | Glenn | A61M 16/026 128/204.23 |

FOREIGN PATENT DOCUMENTS

| | | |
|---|---|---|
| EP | 1525893 A2 | 4/2005 |
| EP | 2022525 A1 | 2/2009 |
| EP | 2119465 A1 | 11/2009 |
| WO | WO9424935 A1 | 11/1994 |
| WO | WO2004045689 A1 | 6/2004 |

* cited by examiner

CONTROL DEVICE FOR A MEDICAL AEROSOL DELIVERY DEVICE

CROSS-REFERENCE TO RELATED APPLICATIONS

This patent application claims the priority benefit under 35 U.S.C. § 371 of international patent application no. PCT/EP2016/065188, filed Jun. 29, 2016, which claims the benefit of European Patent Application No. 15174429.9, filed on Jun. 30, 2015, the contents of which are herein incorporated by reference.

FIELD OF THE INVENTION

The invention relates to a control device for a medical aerosol delivery device, a medical aerosol delivery system, a method for controlling a medical aerosol delivery device, a computer program element for controlling such device or system, and a computer readable medium having stored such computer program element.

BACKGROUND OF THE INVENTION

EP 1 525 893 A2 discloses a drug delivery apparatus in form of a nebulizer. The nebulizer comprises means for determining a duration of a pulse of atomisation during inspiration, such means including means for measuring the patient's tidal volume, timing means for measuring the duration of inspiration, means for storing an estimate of the volume of the patient's upper airway and means for calculating the duration of the pulse on the basis of the measurements and stored estimate. An alternative nebuliser comprises means for predicting the tidal volume including means for measuring the patient's peak flow, timing means for measuring duration of inspiration and means for calculating the tidal volume on the basis of the measurements; and means for atomising a medication, means for monitoring the patient's breathing pattern and means for controlling the atomising means to provide pulses of varying length and proportion of the inspiratory phase in dependence on the breathing pattern.

Such conventional nebulizers or medical aerosol delivery devices comprise a control unit to implement an adaptive aerosol delivery algorithm to control a timing of aerosol drug delivery into a user's or patient's breathing pattern. A conventional adaptive aerosol delivery algorithm treats also brief periods of inhalation flow as breaths for the purpose of predicting a length of a next breath. Such brief periods of inhalation flow can, however, be breathing pattern anomalies that can be caused for example by patients consciously trying to control a transition between inhalation and exhalation or by moving their tongues across a mouthpiece before a start of a true inhalation.

If a patient's breathing pattern is such that it has these breathing anomalies, a proportion of time per breath spent delivering aerosol will be reduced and an overall treatment time will be increased. Increased treatment time is, however, associated with poor treatment regimen compliance.

U.S. Pat. No. 5,201,322 discloses a device for detecting the presence and direction of air flow through a passageway with a first and a second opening for airflow therethrough. The device comprises a piezoelectric sensor located within the passageway. The sensor generates a first electrical signal when air flows through the passageway in a first direction and a second electrical signal when air flows through the passageway in a second direction, opposite to the first direction.

US 2005/0183725 A1 discloses a fluid sensor to activate and control various components of an inhalation device. The sensor includes an acoustic element positioned within the inhalation device to detect fluid within the device and output signals representative of the frequency, direction and/or amplitude of the fluid. These signals control and activate an electrostatic plate and/or a high frequency vibrator.

U.S. Pat. No. 5,944,680 discloses a method of predicting critical points in patient respiration. The method includes monitoring at least one characteristic of a respiratory effort waveform of a patient to detect a respiratory event. The respiratory event may be inspiration onset and the characteristic of the respiratory effort waveform monitored is at least one of slope and amplitude. Stimulation may be provided in response to a detected inspiration onset.

EP 765 631 A2 discloses an apparatus for monitoring the respirations of a patient. The apparatus comprises generating means for generating a respiration signal having amplitude modulations representative of patient respirations, as well as respiration artifacts, and processing means coupled to the generating means and responsive to the respiration signal.

U.S. Pat. No. 6,537,228 B1 discloses a method and an apparatus in an apnea detector, which monitor impedance pneumographic respiratory signals and the heart rate of a patient. Magnitudes of excursions of the respiratory signals are monitored to resolve respiratory events, i.e. breath, inhalations and exhalations.

SUMMARY OF THE INVENTION

Hence, there may be a need to provide an improved control device for a medical aerosol delivery device, which in particular allows reducing treatment times. The problem of the present invention is solved by the subject-matters of the independent claims, wherein further embodiments are incorporated in the dependent claims.

It should be noted that the aspects of the invention described in the following apply also to the control device for a medical aerosol delivery device, the medical aerosol delivery system, the method for controlling a medical aerosol delivery device, the computer program element, and the computer readable medium.

According to the present invention, a control device for a medical aerosol delivery device is presented. The control device comprises a provision unit, a processing unit and a control unit. The provision unit is configured to provide inhalation length data per breath. The processing unit is configured to compare the provided inhalation length data with a predetermined inhalation length threshold, and to filter provided inhalation length data below the predetermined inhalation length threshold. The control unit is configured to control the medical aerosol delivery device based on the filtered inhalation length data.

The provided inhalation length data per breath may comprise or may be understood as one or several measured breathing signal(s), breathing value(s), inhalation duration(s), inhalation length(s) or inhalation time(s).

The comparison of the provided inhalation length data with the predetermined inhalation length threshold may be understood as a detection of artifacts and/or spikes in inhalation length data. The artifacts and/or spikes may be understood as short breaths and/or breathing pattern anomalies caused e.g. by a user consciously trying to control a transition between inhalation and exhalation or by moving his/her tongue across a mouthpiece before a start of a true inhalation or the like.

The predetermined inhalation length threshold may be between 50 ms and 1000 ms or between 100 ms to 400 ms or may be about 250 ms.

The filtered inhalation length data are data obtained after the provided inhalation length data were filtered.

The control device for a medical aerosol delivery device according to the invention allows reducing treatment times. This is achieved as the control device may implement an algorithm to control a timing of aerosol drug delivery into a user's breathing pattern. Thereby, the control device may prevent short periods of inhalation flow from reducing the time spent nebulising into patient breaths and thereby increasing an overall treatment time. In other words, this invention prevents the algorithm from shortening aerosol delivery periods as a result of brief inhalation periods and/or breathing pattern anomalies caused by e.g. consciously controlling a transition between inhalation and exhalation or by moving a tongue across a mouthpiece of a medical aerosol delivery device or the like. The benefit is that overall treatment times are kept short and good treatment regimen compliance is promoted.

This is achieved as artifacts and/or spikes in inhalation length data are managed in an improved manner. This means, these artifacts are detected and filtered. Such artifact may be detected when the inhalation length data is e.g. in a range of 50 ms to 1000 ms and preferably amounts to only 250 ms. The filtering may comprise an ignoring of the inhalation length data or a replacing of the inhalation length data by a previous moving average value. In other words, this invention prevents periods of inhalation flow less than, for example 250 ms, from being included in a prediction of a length of a next breath and a setting of aerosol delivery duration into the next breath.

The filtering may be a removing or ignoring of provided inhalation length data below the predetermined inhalation length threshold. The filtering may also be a replacing of provided inhalation length data below the predetermined inhalation length threshold by a database value, an average value or moving average value of a previous breath. Therefore, the processing unit may be configured to process the provided inhalation length data into a previous moving average value per breath. Replacing provided inhalation length data below the predetermined inhalation length threshold by a moving average value of the previous breath eliminates the chance that the calculation would crash if there were consecutive breaths of less than the threshold.

The previous moving average value may be e.g. a three-breath-moving average value. The moving average value can also be based on any other number of breaths, as e.g. a five-breath-moving average value, or weighted to remove the influence of older breaths, e.g. exponentially weighted moving average. When e.g. a number of inhalations, n, is greater than three, the three-breath moving average, $\tau$, may be calculated by summing the inhalations lengths for the previous three breaths and dividing by three. For instances, where the inhalation length is less than a predetermined inhalation length threshold of e.g. 250 ms, this inhalation length is replaced by the previous moving average value, $\tau_j$. In the below example, all times are taken to be greater than 250 ms:

$$\tau_n = \frac{t_{n-3} + t_{n-2} + t_{n-1}}{3}, \ t_{n-3}, t_{n-2}, t_{n-1} > 250 \text{ ms}$$

When one provided or measured inhalation length $\tau$ is less than 250 ms, e.g. $t_{n-2}$, the three breath moving average will be calculated using $$\tau_n = \frac{t_{n-3} + \tau_{n-2} + t_{n-1}}{3}, \ t_{n-3}, t_{n-1} > 250 \text{ ms} > t_{n-2}$$

where the three-breath moving average value at inhalation number n-2 is used to replace measured inhalation length $t_{n-2}$ that is less than 250 ms.

The three-breath moving average, $\tau$, is used to calculate the length of time that aerosol will be delivered into the next breath. The control device according to the invention may be used for an adaptive aerosol delivery for high end nebulizers such as Philips Ineb. The medical aerosol delivery device may be a mesh based nebulizer.

In an example, the control unit is configured to calculate a predicted inhalation time for a user's subsequent inhalation based on the filtered inhalation length data.

In an example, the control unit is further configured to calculate a target aerosol pulse length for the user's subsequent inhalation based on the filtered inhalation length data.

In an example, the provision unit is further configured to provide inhalation flow data, and wherein the processing unit is further configured to filter when the provided flow data is approximately zero to average flow data.

According to the present invention, also a medical aerosol delivery system is presented. The medical aerosol delivery system comprises an aerosol delivery device and a control device as described above. The control device is configured to control the aerosol delivery device. The aerosol delivery device is configured to deliver aerosol to a user. The aerosol delivery device may be an adaptive aerosol delivery device for high end nebulizers such as Philips Ineb. The medical aerosol delivery device may be a mesh based nebulizer.

According to the present invention, also a method for controlling a medical aerosol delivery device is presented. The method comprises the following steps, not necessarily in this order:

providing inhalation length data per breath, comparing the provided inhalation length data with a predetermined inhalation length threshold, filtering the provided inhalation length data below the predetermined inhalation length threshold, and controlling the medical aerosol delivery device based on the filtered inhalation length data.

The method for controlling a medical aerosol delivery device according to the invention allows reducing treatment times and good treatment regimen compliance. This is achieved as artifacts and/or spikes in inhalation length data are detected and filtered. Such artifact may be detected when the inhalation length data is e.g. in a range of 50 ms to 1000 ms. The filtering may comprise an ignoring of the inhalation length data or a replacing of the inhalation length data by a previous moving average value. Thereby, the control device may prevent short periods of inhalation flow from reducing the time spent nebulising into patient breaths and thereby increasing an overall treatment time.

According to the present invention, also a computer program element is presented, wherein the computer program element comprises program code means for causing the control device for a medical aerosol delivery device or the medical aerosol delivery system as defined in the independent device claims to carry out the steps of the method for controlling a medical aerosol delivery device as defined in the independent method claim when the computer program is run on a computer controlling the control device for a medical aerosol delivery device or the medical aerosol delivery system.

It shall be understood that the control device for a medical aerosol delivery device, the medical aerosol delivery system, the method for controlling a medical aerosol delivery device, the computer program element for controlling such device or system, and the computer readable medium having stored such computer program element according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

Figure 1:
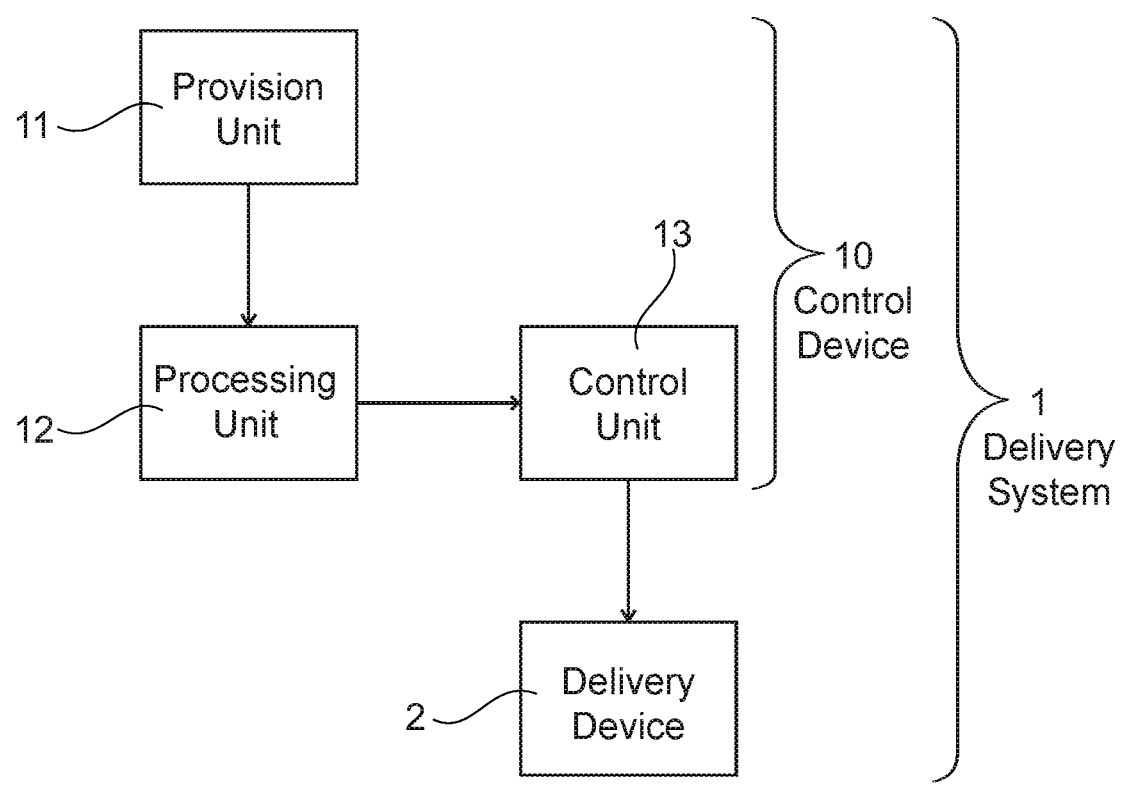
FIG. 1 shows a schematic drawing of an example of a medical aerosol delivery system.

FIG. 1 shows schematically and exemplarily an embodiment of a medical aerosol delivery system 1. The medical aerosol delivery system 1 comprises an aerosol delivery device 2 and a control device 10. The aerosol delivery device 2 is configured to deliver aerosol to a user. The control device 10 is configured to control the aerosol delivery device 2. The control device 10 therefore comprises a provision unit 11, a processing unit 12, and a control unit 13. The provision unit 11 is configured to provide inhalation length data per breath. The processing unit 12 is configured to compare the provided inhalation length data with a predetermined inhalation length threshold, and to filter provided inhalation length data below the predetermined inhalation length threshold. The control unit 13 is configured to control the medical aerosol delivery device 2 based on the filtered inhalation length data.

The medical aerosol delivery system 1 and the control device 10 for a medical aerosol delivery device 2 according to the invention allow reducing treatment times. This is achieved as the control device 10 may implement an algorithm to control a timing of aerosol drug delivery into a user's breathing pattern. Thereby, the control device 10 may prevent short periods of inhalation flow from reducing the time spent nebulising into patient breaths and thereby increasing an overall treatment time.

In an example, the predetermined inhalation length threshold is between 50 ms and 1000 ms. In a further example, the predetermined inhalation length threshold is 100 ms to 400 ms. In another example, the predetermined inhalation length threshold is 250 ms. In an example, the filtering is a removing of provided inhalation length data below the predetermined inhalation length threshold.

In another example, the processing unit 12 is further configured to process the provided inhalation length data into a three-breath-moving average value per breath, wherein the filtering is a replacing of provided inhalation length data below the predetermined inhalation length threshold by a three-breath-moving average value of the previous breath.

Figure 2:
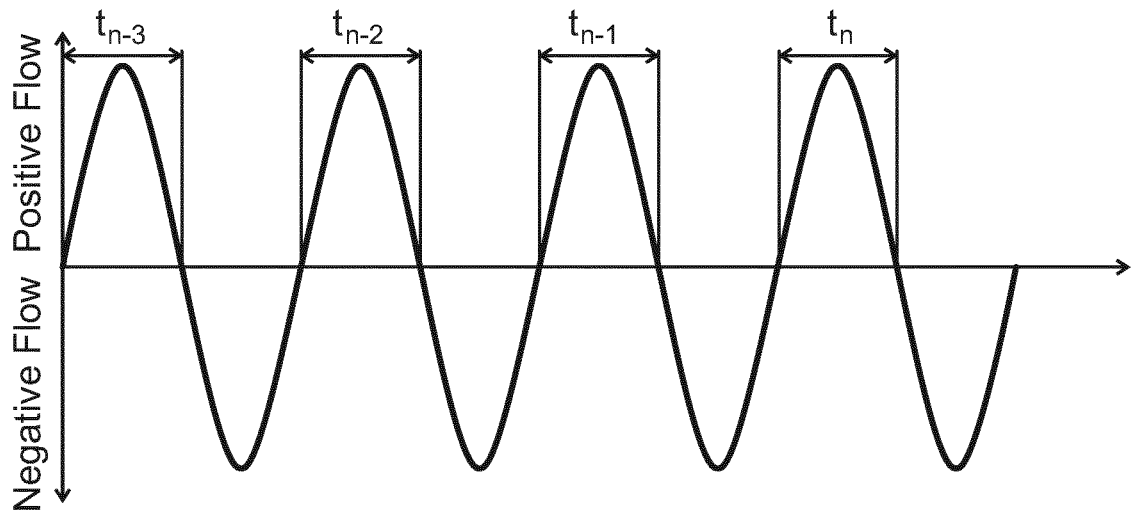
FIG. 2 shows a sequence of four breaths with each breath having an inhalation length of $t_x$ seconds all of which are greater than 250 ms.
Figure 3:
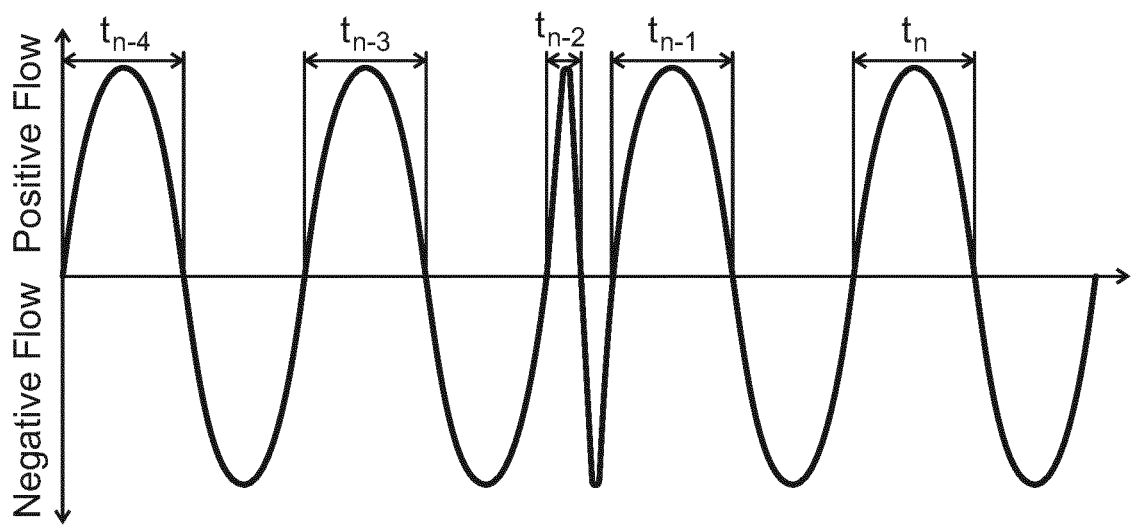
FIG. 3 shows a sequence of five breaths with one breath having an inhalation length of less than 250 ms.

In FIGS. 2 and 3, the previous moving average value is a three-breath-moving average value. When e.g. a number of inhalations, n, is greater than three, the three-breath moving average, τ, is calculated by summing the inhalations lengths for the previous three breaths and dividing by three. In this example, where the inhalation length is less than a predetermined inhalation length threshold of 250 ms, this inhalation length is replaced by the previous moving average value, $\tau_j$. In the example of FIG. 2, all times are taken to be greater than 250 ms:

$$\tau_n = \frac{t_{n-3} + t_{n-2} + t_{n-1}}{3}, \ t_{n-3}, t_{n-2}, t_{n-1} > 250 \text{ ms}$$

In FIG. 3, when one provided or measured inhalation length $t_{n-2}$ is less than 250 ms, the three breath moving average is calculated using $$\tau_n = \frac{t_{n-3} + \tau_{n-2} + t_{n-1}}{3}, \ t_{n-3}, t_{n-1} > 250 \text{ ms} > t_{n-2}$$

where the three-breath moving average value T at inhalation number n-2 is used to replace measured inhalation length $t_{n-2}$ that is less than 250 ms.

The three-breath moving average, τ, is used to calculate the length of time that aerosol will be delivered into the next breath.

Figure 4:
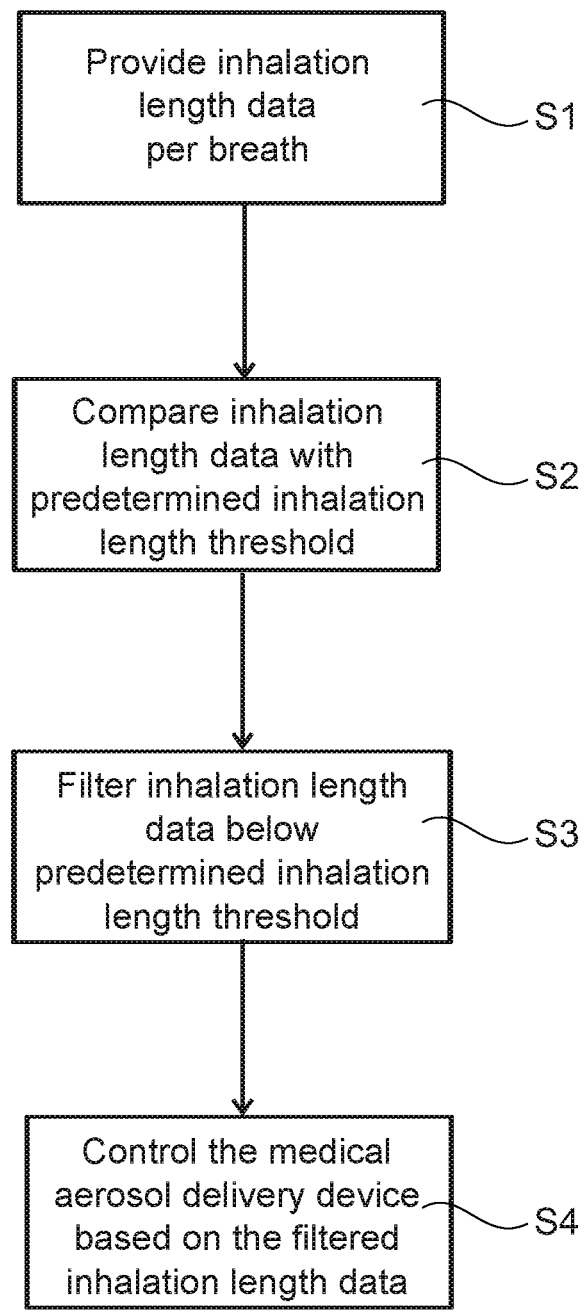
FIG. 4 shows basic steps of an example of a method for controlling a medical aerosol delivery device.

FIG. 4 shows a schematic overview of steps of a method for controlling a medical aerosol delivery device 2. The method comprises the following steps, not necessarily in this order:

In a first step S1, providing inhalation length data per breath.

In a second step S2, comparing the provided inhalation length data with a predetermined inhalation length threshold.

In a third step S3, filtering the provided inhalation length data below the predetermined inhalation length threshold.

In a fourth step S4, controlling the medical aerosol delivery device 2 based on the filtered inhalation length data.

In an example, the medical aerosol delivery device 2 calculates a predicted inhalation time for a user's subsequent inhalation based on the filtered inhalation length data. In an example, the medical aerosol delivery device 2 calculates a target aerosol pulse length for the user's subsequent inhalation based on the filtered inhalation length data.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it, which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A method for controlling a medical aerosol delivery device, the method comprising:
   providing inhalation duration data per breath,
   comparing, by a processor, the measured inhalation duration data with a predetermined inhalation duration threshold,
   removing, by the processor, the measured inhalation duration data that are below the predetermined inhalation duration threshold,
   processing, by the processor, the provided measured inhalation length duration data into a moving average value per breath,
   replacing, by the processor, the removed inhalation duration data with the moving average value to produce filtered inhalation duration data; and
   controlling, by the processor, a timing of aerosol drug delivery of the medical aerosol delivery device based on the filtered inhalation duration data.

2. The method of claim 1, wherein the predetermined inhalation duration threshold is between 50 ms and 1000 ms.

3. The method of claim 1, wherein the predetermined inhalation duration threshold is between 100 ms and 400 ms.

4. The method of claim 1, wherein the predetermined inhalation duration threshold is 250 ms.

* * * * *